United States Patent [19]

Hotten

[11] 4,118,330

[45] Oct. 3, 1978

[54] AMINE PHOSPHATE SALTS AND PHOSPHORAMIDES

[75] Inventor: Bruce W. Hotten, Orinda, Calif.

[73] Assignee: Chevron Research Company, San Francisco, Calif.

[21] Appl. No.: 858,587

[22] Filed: Dec. 8, 1977

[51] Int. Cl.² .................... C10M 1/44; C10M 3/38; C10M 5/24; C10M 7/24
[52] U.S. Cl. .................... 252/32.5; 252/49.9; 252/400 A; 424/199; 424/211
[58] Field of Search ............. 252/32.5, 49.9, 400 A

[56] References Cited

U.S. PATENT DOCUMENTS

| | | | |
|---|---|---|---|
| 2,371,854 | 3/1945 | Smith et al. | 252/32.5 |
| 2,563,506 | 8/1951 | Werntz | 252/32.5 |
| 3,711,404 | 1/1973 | Redmore | 252/49.9 |
| 3,810,838 | 5/1974 | Hauglon | 252/49.9 |
| 3,992,307 | 11/1976 | Hotten | 252/49.9 |

*Primary Examiner*—Irving Vaughn
*Attorney, Agent, or Firm*—D. A. Newell; C. J. Tonkin; L. L. Vaughan

[57] ABSTRACT

A mixture of phosphate salts and phosphoramides are prepared by reacting a triaryl phosphate and an aliphatic amine in the presence of a catalytic amount of boron trifluoride. These phosphorus mixtures are useful as additives for lubricating oils.

9 Claims, No Drawings

AMINE PHOSPHATE SALTS AND PHOSPHORAMIDES

FIELD OF THE INVENTION

This invention relates to a process for preparing lubricating oil additives and to the products prepared by this process. This invention also relates to lubricating oil compositions containing the products of the process of this invention.

BACKGROUND OF THE INVENTION

Nearly all phosphoramides have been synthesized from phosphoryl chloride and amines. This reaction is adequate for academic research, but it is impractical for commercial production of oil-soluble products, because the water-washing step required for removal of chlorides causes severe emulsification problems.

Amine phosphate salts have been prepared by heating an amine and the corresponding O,O-dihydrocarbyl phosphoric acid. When trialkyl phosphates are reacted with amines, they act as alkylating agents with the product forming as illustrated below, where R and $R^1$ are alkyl:

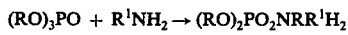

$$(RO)_3PO + R^1NH_2 \rightarrow (RO)_2PO_2NRR^1H_2$$

This type of reaction is illustrated in U.S. Pat. No. 2,563,506.

When R in the above reaction sequence is aromatic, no reaction between the amine and the phosphate occurs.

SUMMARY OF THE INVENTION

It has now been found that phosphoramides can be prepared by methods that require no chloride removal, when a triaryl phosphate and a primary or secondary aliphatic amine are reacted in the presence of boron trifluoride to yield predominantly a phosphoramide of bisphosphoramide along with a minor amount of the amine phosphate salt. Certain of the products prepared by the process of this invention are particularly useful as anti-oxidants, anti-wear agents and friction-modifying additives for lubricating oils.

DETAILED DESCRIPTION OF THE INVENTION

Starting Materials

Preferred triaryl phosphates for use within the scope of this invention are those of the formula

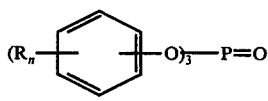

where R is alkyl, halo, alkoxy, nitro, trifluoromethyl, or dihydrocarbylamine and n is 0, 1 or 2.

Preferred primary or secondary aliphatic amines are those in which the aliphatic radical contains from 4 to 18 carbon atoms.

Particularly preferred starting-material phosphates and amines for preparing the lubricating oil additives are those where R is alkyl and the aliphatic amine is a primary alkyl amine containing 12–18 carbon atoms.

As used herein, the following terms have the meaning set forth below.

"Aryl" means a compound containing at least one aromatic, 6-carbon-membered ring. It may contain other cycloaliphatic rings and/or any substituent groups that do not adversely affect the desired reaction path.

"Primary amine" means an amine having two hydrogen substituents and one non-hydrogen substituent that is bonded by a carbon bond to a nitrogen atom.

"Secondary amine" means an amine having one hydrogen substituent and two non-hydrogen substituents that are bonded by a carbon bond to a nitrogen atom.

"Aliphatic" means a non-aromatic, carbon-containing radical which is either saturated or unsaturated, that is contains one or more olefinic or acetylenic sites of unsaturation. The aliphatic radical may not contain any substituents that would adversely affect the reaction of this invention. Preferably the aliphatic group contains only carbon and hydrogen and consists of 3 to 30 carbon atoms.

"Alkyl" means a saturated aliphatic carbon chain of 1 to 30 carbon atoms which contains only carbon and hydrogen atoms.

"Halo" means fluoro, chloro, bromo or iodo.

"Alkoxy" means the radical alkyl-O- where alkyl is as defined above.

"Hydrocarbyl" means a $C_1$-$C_{30}$ aliphatic or $C_6$-$C_{30}$ aromatic hydrocarbon radical containing only carbon and hydrogen atoms.

Reaction Conditions

The reaction is preferably carried out by combining in the reaction mixture from 1 to 20 mols of amine per mol triaryl phosphate. Generally the reaction proceeds most efficiently when the molar ratio of reactants is 2–3 mols of amine per mol of triaryl phosphate.

The reaction usually proceeds to completion in from 0.5 to 30 hours when a reaction temperature of 100°–200° C. is employed.

Excess amine, aromatic by-products and catalyst can be removed, if desired, from the reaction product by vacuum distillation at 100–1000 Pa (0.75–7.5 mm Hg) and a pot temperature of about 100°–170° C.

A catalytic amount of boron trifluoride must be present in the reaction mixture. Preferably 1–5 weight percent based on the total weight of amine and phosphate, and most preferably 3–5 weight percent, boron trifluoride is used as the catalyst.

If desired, the reaction may be carried out in the presence of a hydrocarbon diluent; however, the reaction usually proceeds satisfactorily in the absence of any solvent or diluent.

Uses

The mixtures of phosphorus compounds prepared by the process of this invention have a variety of uses, such as lubricating oil additives, thickening agents, and biocides.

Lubricating Oil Compositions

The preferred mixtures of phosphorus compounds for use in lubricating oil compositions are described above. These mixtures are particularly useful as anti-oxidant, anti-wear and friction-modifying additives for lubricating oils. Their use in oils reduces the power lost between sliding parts and can increase the number of miles per gallon of fuel that an engine can produce.

The lubricating oil compositions of this invention can be prepared by mixing an oil of lubricating viscosity with from 0.01 to 10% by weight of the desired phosphorus compound as additive. The amount of additive which may be present in the lubricating oil in order to impart the desired properties varies with the type of additive, the type of lubricating oil, and the presence of other additives. This type of variation is well known in the art. In general, the preferred additive concentration is 0.05–2% by weight based on the weight of the final lubricating oil composition.

The lubricating oil which may be employed in the practice of this invention includes a wide variety of hydrocarbon oils. Other oils include lubricating oils derived from coal products and synthetic oils, e.g., alkylene polymers (such as polypropylene, polybutylene, etc., and mixtures thereof), alkylene oxide-type polymers (e.g., alkylene oxide polymers prepared by polymerizing alkylene oxides such as propylene oxide, etc., in the presence of water or alcohol, e.g., ethyl alcohol), carboxylic acid esters (e.g., those which were prepared by esterifying carboxylic acids such as adipic acid, azelaic acid, suberic acid, sebacic acid, alkenylsuccinic acid, fumaric acid, maleic acid, etc., with the alcohol such as butyl alcohol, hexyl alcohol, 2-ethylhexyl alcohol, pentaerythritol, etc., liquid esters of phosphorus, such as trialkyl phosphate (tributyl phosphate), dialkylaryl phosphate, triaryl phosphate (tricresyl phosphate), etc., alkylbenzenes, polyphenols (e.g., bisphenols and terphenols), alkylbiphenylethers, esters and polymers of silicon, e.g., tetraethyl silicate, tetraisopropyl silicate, hexyl-(4-methyl-2-pentoxy) disilicate, poly(methyl)siloxane and poly(methylphenyl)siloxane, etc. The lubricating oils may be used individually or in combinations whenever miscible or whenever made so by use of mutual solvents. The lubricating oils generally have a viscosity which ranges from 50 to 5000 SUS (Saybolt Universal Seconds) and usually from 100 to 1500 SUS at 100° F. (38° C.).

In addition to the phosphate salt, other additives may be successfully employed within the lubricating compositions of this invention without affecting their high stability and performance over a wide temperature scale. One type of additive is an anti-oxidant or oxidation inhibitor. This type of additive is employed to prevent varnish and sludge formation on metal parts and to inhibit corrosion of alloyed bearings. Typical anti-oxidants are organic compounds containing sulfur, phosphorus or nitrogen, such as organic amines, sulfides, hydroxysulfides, methanols, etc., alone or in combination with metals such as zinc, tin or barium. Particularly useful anti-oxidants include phenyl-alpha-naphthylamine, bis(alkylphenyl)amine, N,N'-diphenyl-p-phenylenediamine, 2,2,4-trimethyldihydroquinoline oligomer, bis(4-isopropylaminophenyl) ether, N-acylaminophenol, N-acylphenothiazines, N-hydrocarbylamides of ethylenediamine tetraacetic acid, alkyl-phenol-formaldehyde-amine polycondensates, etc.

Another additive which may be employed is a rust inhibitor. The rust inhibitor is employed in all types of lubricants to suppress the formation of rust on the surface of metallic parts. Exemplary rust inhibitors include sodium nitrite, alkenylsuccinic acids and derivatives thereof, alkylthioacetic acid and derivatives thereof, substituted imidazoles, amine phosphates, etc. Another additive which may be incorporated into the lubricant composition of this invention is an anti-corrodant. The anti-corrodant is employed to inhibit oxidation so that the formation of acidic bodies is suppressed and to form films over the metal surfaces which decrease the effect of corrosive materials on exposed metallic parts. Typical anti-corrodants are organic compounds containing active sulfur, phosphorus or nitrogen, such as organic sulfides, phosphides, metal salts of thiophosphoric acid, cyclic and acyclic epoxides and sulfurized waxes, barium phenates and sulfonates, etc. A particularly effective corrosion inhibitor is ammonium dinonylnaphthylene sulfonate.

Other types of lubricating oil additives which may be employed in the practice of this invention include anti-foam agents (e.g., silicones, organic copolymers), stabilizers, anti-stain agents, tackiness agents, anti-chatter agents, dropping point improvers, anti-squawk agents, lubricating color correctors, extreme-pressure agents, odor control agents, dispersants, detergents, etc., as well as other anti-wear agents such as tricresyl phosphate and zinc dithiophosphate esters.

In many instances, it may be advantageous to form concentrates of the reaction product of this invention within a carrier liquid. The employment of concentrates provides a convenient method of handling and transporting the reaction products for their subsequent dilution and use. The concentration of the reaction product within the concentrates may vary from 10 to 90 weight percent, although it is preferred to maintain the concentration between about 20 and 80 weight percent.

ILLUSTRATIVE EXAMPLE

To a 1-liter flask was added 109 g (⅓ mol) triphenyl phosphate and 215 g (1 mol) cocoamine (96% n-dodecylamine). The reaction mixture was heated with stirring at 150° C. under nitrogen for 4 hours. Analysis by infrared at the end of 4 hours indicated that little to no reaction had taken place.

EXAMPLE 1

To a reaction vessel was added 326.3 g (1 mol) triphenyl phosphate in 215 g (1 mol) n-dodecylamine (98% pure) and 27 g (5% by weight) of boron trifluoride in phenol. The reaction mixture was stirred at 150° C. for 4 hours. The product contained 7.0% P and 3.1% N and had an acid number of 39 mg KOH/g and alkalinity value of 1 mg KOH/g.

EXAMPLE 2

To a 2-liter reaction flask was added 430 g (2 mols) cocoamine (96% n-dodecylamine), 326.3 g (1 mol) triphenyl phosphate, and 37.8 g (5% by weight) of boron trifluoride etherate. The reaction mixture was heated to 150° C. for 4 hours and then stripped to 150° C. at 4 mm Hg, to yield 768.9 g of product. Analysis: 5.9% P, 3.4% N, acid number 34 mg KOH/g, alkalinity value 15 mg KOH/g.

The product distribution obtained in Examples 1 and 2 is noted in Table I below, where the structure of the products was determined by phosphorus nuclear magnetic resonance.

TABLE I

| Product | Molar percentage distribution in final product prepared in Example | |
|---|---|---|
| | 1 | 2 |
| $\phi O-P(=O)-(NHR)_2$ | 3 | 12 |
| $(\phi O)_2-P(=O)-NHR$ | 73 | 76 |
| $(\phi)_2-P-O_2NH_3R$ (salt) | 5 | 5 |

TABLE I-continued

| Product | Molar percentage distribution in final product prepared in Example | |
|---|---|---|
| | 1 | 2 |
| $(\phi O)_3$—P=O (starting material)  | 11 | 1 |

EXAMPLE 3

The coefficient of friction of a lubricating oil containing the additive prepared by the process of Example 2 was tested in the Kinetic Oiliness Testing Machine (KOTM) manufactured by G. L. Neeley of Berkeley, Calif. The procedure used in this test is described by G. L. Neeley, Proceeding of Mid-Year Meeting, American Petroleum Institute, 1932, pp. 60–74. Friction was measured in this test under boundary conditions with a load of 100 pounds (12 MPa), speed of 0.1 rpm (0.5 mm/sec). The oil being tested in an SAE 10W40 oil containing 8.4% of a polyacrylate viscosity index improver and also containing a conventional polybutene succinimide dispersant, zinc dialkyl dithiophosphate and overbased magnesium sulfonate. The results in Table II below show good reduction in the coefficient of friction on both metal combinations tested and at all temperatures tested.

TABLE II
Effect of Product of Example 3 on Coefficient of Friction

| Metal Surfaces | Wt. % Product of Ex. 2 | Coefficient of Friction at | | | |
|---|---|---|---|---|---|
| | | 50 °C | 100 °C | 150 °C | 200 °C |
| Chromium sliders on Cast Iron Track | 0 | 0.13 | 0.13 | 0.13 | 0.14 |
| | 1 | 0.13 | 0.12 | 0.12 | 0.12 |
| 52100 Steel Sliders on Cast Iron Track | 0 | 0.14 | 0.13 | 0.13 | 0.15 |
| | 1 | 0.12 | 0.11 | 0.11 | 0.12 |

What is claimed is:

1. A process comprising heating a triaryl phosphate and a primary or secondary aliphatic amine in the molar ratio of 1:1–20 respectively, at a temperature of 100°–200° C. for 0.5 to 30 hours in the presence of a catalytic amount of boron trifluoride to yield a mixture comprising a major proportion of phosphoramide and a minor proportion of phosphate salt.

2. The process of claim 1 wherein the triaryl phosphate has the formula

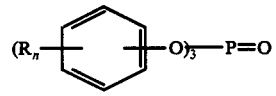

where R is alkyl, halo, alkoxy, nitro, trifluoromethyl, or dihydrocarbyl amino, n is 0, 1 or 2, and the aliphatic amine has the formula $$R^1NR^2$$
$$H$$

where $R^1$ is an aliphatic radical containing 4–18 carbon atoms and $R^2$ is hydrogen or an aliphatic radical containing 4–18 carbon atoms, and 1–5 weight percent boron trifluoride is employed.

3. The process of claim 2 wherein 3–5% by weight of boron trifluoride is used as the catalyst and the molar ratio of phosphate to amine is about 1:2–3, and $R^2$ is hydrogen.

4. The process of claim 3 wherein R is alkyl, $R^1$ is alkyl of 12–18 carbon atoms, and $R^2$ is hydrogen.

5. The product prepared by the process of claim 1.

6. The product prepared by the process of claim 4.

7. A lubricating oil composition comprising an oil of lubricating viscosity and from 0.01 to 10% by weight of the product of claim 6.

8. A lubricating oil concentrate comprising from 10–90% by weight of an oil of lubricating viscosity and from 90–10% by weight of the product of claim 6.

9. A method for reducing the friction between relatively moving parts comprising lubricating said parts with the lubricating oil composition of claim 7.

* * * * *